(12) United States Patent
Albers et al.

(10) Patent No.: US 6,449,510 B1
(45) Date of Patent: Sep. 10, 2002

(54) METHOD AND SYSTEM FOR OPERATING AN IMPLANTABLE MEDICAL DEVICE

(75) Inventors: Bert A. Albers, Woursveld; Willem Boute, Dieren, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/559,049

(22) Filed: Apr. 27, 2000

(51) Int. Cl.[7] ............................................... A61N 1/365
(52) U.S. Cl. ......................................... 607/25; 600/516
(58) Field of Search ............................. 600/516; 607/9, 607/25

(56) References Cited

U.S. PATENT DOCUMENTS

| | | |
|---|---|---|
| 4,303,075 A | 12/1981 | Heilman et al. |
| 4,467,807 A | 8/1984 | Bornzin |
| 4,527,568 A | 7/1985 | Rickards |
| 4,539,991 A | 9/1985 | Boute et al. |
| 4,554,921 A | 11/1985 | Boute et al. |
| 4,686,987 A | 8/1987 | Salo et al. |
| 4,920,965 A | 5/1990 | Funke et al. |
| 4,951,667 A | 8/1990 | Markowitz et al. |
| 4,956,524 A | 9/1990 | Baker |
| 5,330,511 A * | 7/1994 | Boute |

\* cited by examiner

*Primary Examiner*—Scott M. Getzow
(74) *Attorney, Agent, or Firm*—Thomas F. Woods; Thomas G. Berry

(57) ABSTRACT

A method of operating an implantable medical device is provided. A plurality of atrio-ventricular (AV) measurement signals is received. A QT interval is determined. The QT interval is a function of the AV measurement signals. Each of the plurality of AV measurement signals is compared with the QT interval. Finally, if one of the plurality of AV measurement signals is less than the QT interval, a difference between the one of the plurality of AV measurement signals and the QT interval is stored.

42 Claims, 8 Drawing Sheets

METHOD AND SYSTEM FOR OPERATING AN IMPLANTABLE MEDICAL DEVICE

FIELD OF THE INVENTION

The present invention relates to dual chamber cardiac pacemakers and pacemaker systems and, more particularly, to the operation of an implantable dual chamber pacemaker having the capability to inform if a predetermined condition has occurred.

BACKGROUND OF THE INVENTION

The advantages of dual chamber pacing, and more particularly pacing in different modes which are selected in response to different patient conditions, is now well recognized in the art. Early pacing systems were solely ventricular, and were sufficient for management of patient with complete heart block and Stokes-Adams attacks. However, ventricular demand pacemakers are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (AV) interval. Such a pacemaker, e.g. VDI or VDD, allows the atrium to control the heart's response rate, the ventricle being paced at the atrial rate up to a predetermined upper rate limit. Such synchronous pacers have incorporated means for dealing with high atrial rates, including "block" and "Wenckebach" techniques.

Another form of A-V or dual chamber pacer that has been utilized is the sequential pacemaker (DVI), which paces both the atrium and the ventricle with an appropriate AV delay which is timed by the pacemaker. A number of commercial pacemakers have been introduced which are programmable to these and other known pacing modes. Each of the various operating modes is particularly adapted to certain circumstances that may arise in a given patient.

Since the dual sense-dual pace DDD pacemaker became commercially available, it has gained favor for the reason that it compensates for many of the disadvantages of other pacemaker modes. The classic DDD pacemaker is described in U.S. Pat. No. 4,920,965, Funke et al., in some detail. See also U.S. Pat. Nos. 4,539,991 and 4,554,921, incorporated herein by reference, which disclose other forms of DDD-type pacemakers.

More recently, the DDDR pacemaker has come to prominence. In this type of pacemaker, there is provided one or more sensors which enable the pacemaker to be rate responsive, such that the pacing interval, or escape interval, is varied as a function of one or more sensed rate-indicating parameters, rather than being fixed at a programmed value. In the DDDR pacemaker, both atrial and ventricular natural beats may occur so long as they occur prior to the respective rate responsive escape interval. See U.S. Pat. Nos. 4,467,807 and 4,951,667, which are illustrative of dual chamber rate responsive pacemakers.

There have also been disclosed multi-mode pacemaker designs having means for switching modes in response to changing patient conditions. Most dual chamber pacemakers are programmable to distinct modes, or switch automatically from one mode to another under certain prescribed conditions. See, for example, U.S. Pat. Nos. 4,527,568, and 4,920,965. However, as a general rule it is desirable to operate in a synchronized mode as much as possible, wherein an atrial sense (AS) is followed by a ventricular pace pulse (VP) which is timed to occur at an AV interval, or delay, after the AS. Likewise, if the pacemaker is operating in a mode where it is delivering both paced atrial and ventricular pace pulses, it is desired to have the VP follow the atrial pulse (AP) by an optimized AV interval.

It is known in the prior art that it is desirable to set the AV interval as a function of rate, e.g., as a function of sensed atrial rate or pacing rate. See U.S. application Ser. No. 830,656, Dual Chamber Pacemaker With AV Extension and PMT Control, filed Feb. 4, 1992 and assigned to the same assignee as this application; and Baker, U.S. Pat. No. 4,856,524. Thus, at lower atrial rates (corresponding to a longer A-A interval) the AV interval is desirably longer; and at higher atrial rates (corresponding to a shorter A-A interval) the AV interval is preferably shorter. Further, it is known in the prior art that pacing parameters such as AV interval can be programmed externally.

The prior art also shows an attempt to adjust AV interval in a pacemaker as a function of a sensed variable. See U.S. Pat. No. 4,303,075, wherein AV delay is modified in accordance with a sensed measure of stroke volume. However, this disclosure deals with a fixed rate pacer, and does not suggest how AV delay can be optimzied for a rate adaptive pacer. U.S. Pat. No. 4,686,987 discloses a technique for determining stroke volume and for controlling pacing rate as a function of stroke volume, but makes no suggestion of how to adjust AV delay in a rate adaptive pacer. There thus has remained a need for a pacing system that is capable of dynamic automatic adjustment of AV delay, i.e., a DDDR system where AV delay is adjustable through the pacing rate range.

Finally, in U.S. Pat. No. 5,330,511, issued to Boute, there is disclosed a dual chamber system and method of operation containing an automatic test for determining an optimum AV interval at a predetermined test frequency. In performance, the test, which is carried out at nighttime, involves the implanted pacer set to an asynchronous operation at a test frequency (e.g., LRL), and wherein the AV interval is sequenced through a range from a predetermined minimum to a predetermined maximum. The QT interval corresponding to each respective AV interval is determined and stored. The QT data is then analyzed to determine the maximum QT interval. Finally, the optimum AV is determined at that which corresponds to the maximum QT.

As discussed above, the most pertinent prior art patents are:

TABLE 1

Prior Art Patents.

| U.S. Pat. No. | Date | Inventor(s) |
| --- | --- | --- |
| 4,303,075 | 12-01-81 | Heilman et al. |
| 4,467,807 | 05-26-87 | Sanno |
| 4,527,568 | 07-09-85 | Rickards |
| 4,539,991 | 09-10-85 | Boute et al. |
| 4,554,921 | 11-26-85 | Boute et al. |
| 4,686,987 | 08-18-87 | Salo et al. |
| 4,956,524 | 09-11-90 | Baker |
| 4,920,965 | 05-01-90 | Funke et al. |
| 4,951,667 | 08-28-90 | Markowitz et al. |
| 5,330,511 | 07-19-94 | Boute |

All patents listed in Table 1 are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed in the patents of Table 1 may be modified advantageously by using the teachings of the present invention.

SUMMARY OF THE INVENTION

The present invention is therefore directed to providing a method for operating an implantable medical device. Such a system of the present invention overcomes the problems, disadvantages and limitations of the prior art described above, and provides a more efficient and accurate means of operating an implantable medical device.

The present invention has certain objects. That is, various embodiments of the present invention provide solutions to one or more problems existing in the prior art respecting the operation of an implantable medical device. Those problems include, without limitation: comparing a plurality of AV measurement signals with a determined QT interval, and storing a plurality of differences between each the plurality of AV measurement signals and the QT interval if one of the AV measurement signals is less than the QT interval.

In comparison to known techniques for operating an implantable medical device, various embodiments of the present invention may provide one or more of the following advantages: comparing a plurality of AV measurement signals with a determined QT interval, and storing a plurality of differences between each the plurality of AV measurement signals and the QT interval if one of the AV measurement signals is less than the QT interval.

Some of the embodiments of the present invention include one or more of the following features: an implantable medical device including a processor, a memory location operably connected to the processor, a controller operably connected to the processor and at least one sensing lead operably connected to the controller, wherein a difference between one of a plurality of atrio-ventricular (AV) measurement signals and a QT interval is stored in the memory location for each of the plurality of AV measurement signals received by the processor via the at least one sensing lead that is shorter than the QT interval.

Furthermore, in accordance with the present invention, a method of operating an implantable medical device is provided. A plurality of atrio-ventricular (AV) measurement signals is received. A QT interval is determined. The QT interval is a function of the AV measurement signals. Each of the plurality of AV measurement signals is compared with the QT interval. Finally, if one of the plurality of AV measurement signals is less than the QT interval, a difference between the one of the plurality of AV measurement signals and the QT interval is stored.

Therefore, the algorithm of the present invention enables an operation of the implantable medical device in which the device compares two sets of interval values, and stores one set of the values for future use. In this way, it is possible to more accurately plan for future possible heart problems.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

Figure 1:
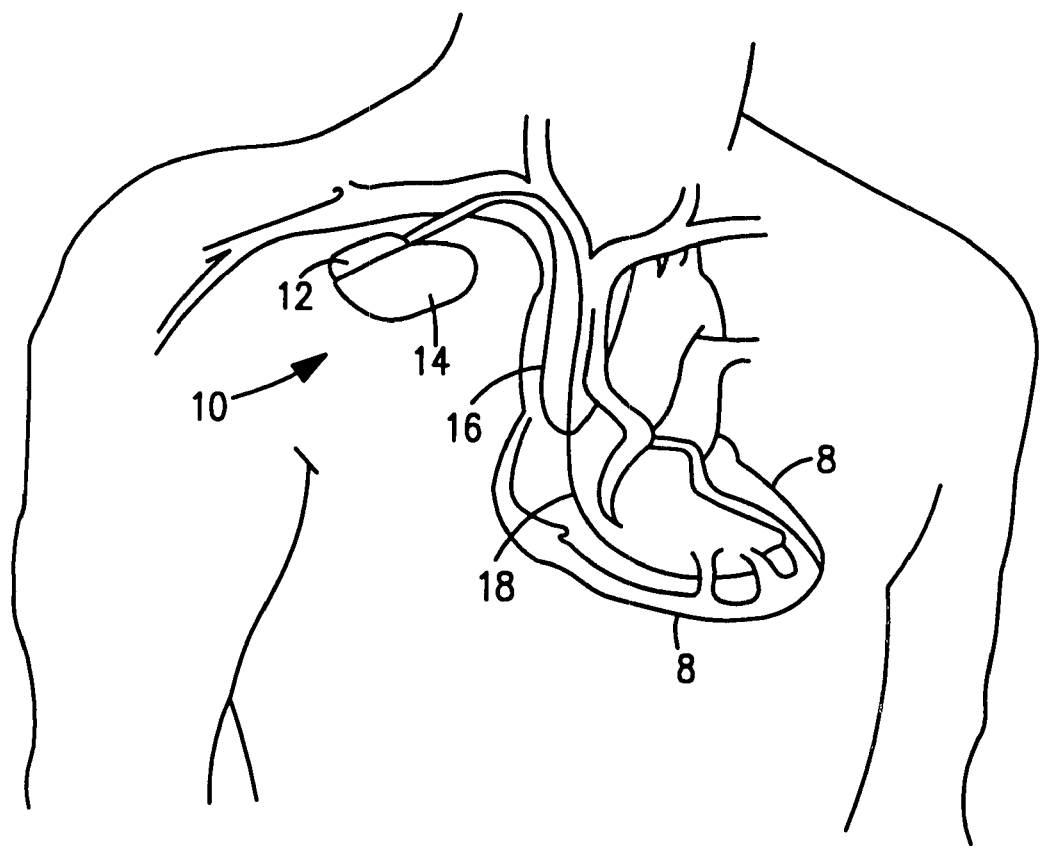
FIG. 1 is a schematic view of an implantable medical device, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
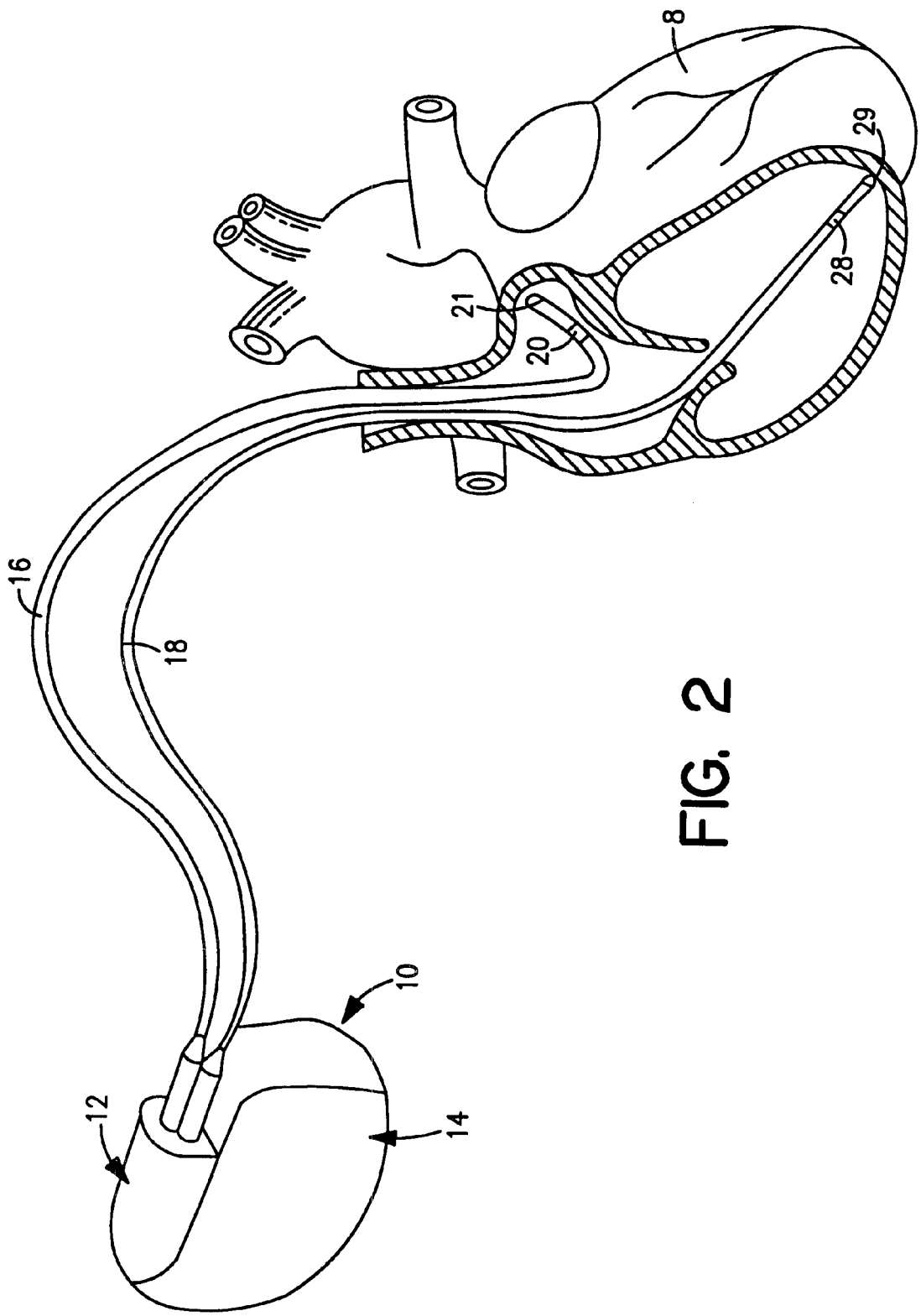
FIG. 2 is another view of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
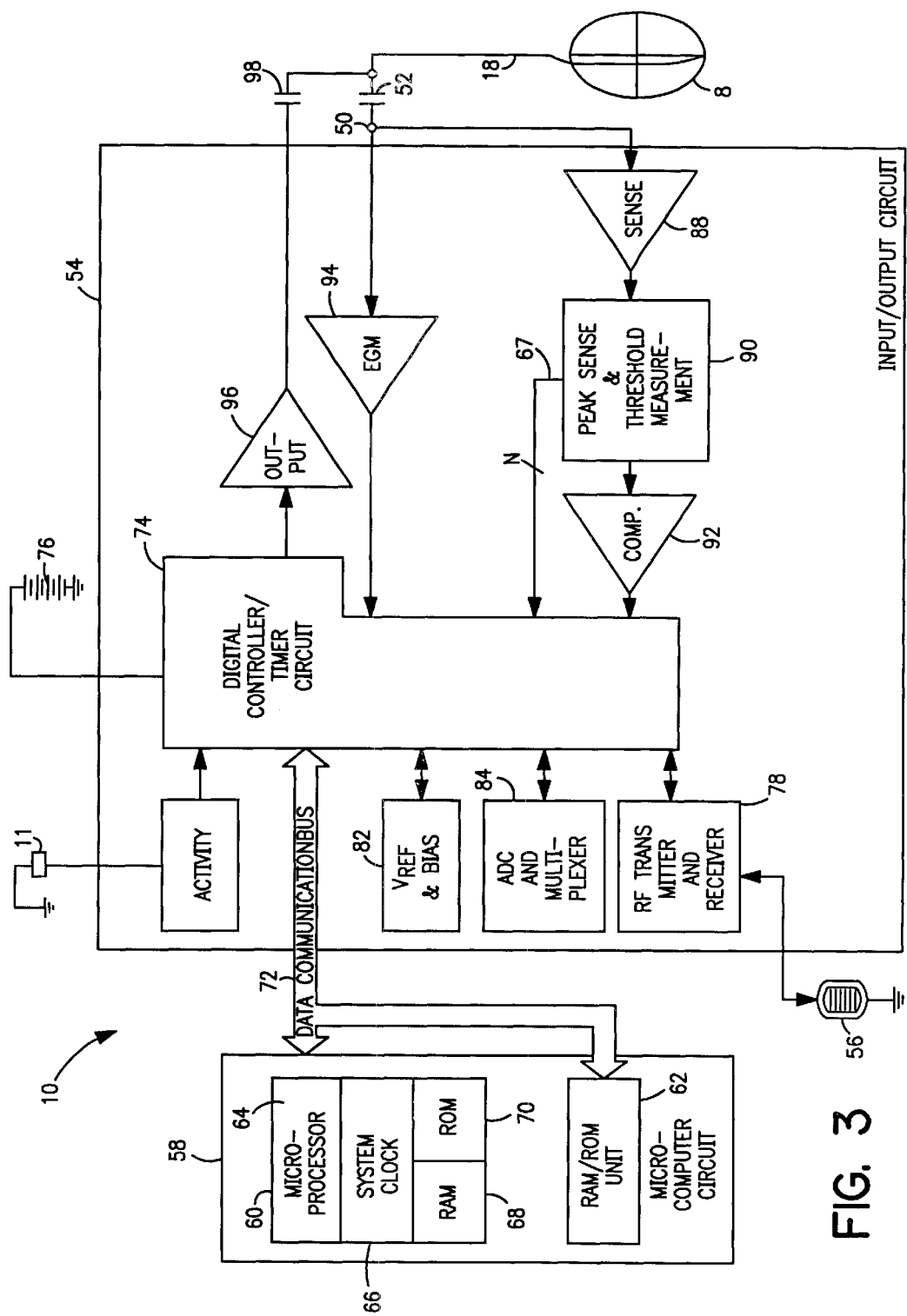
FIG. 3 shows a block diagram illustrating the components of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a processor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is processor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes processor 64, system clock circuit 66 and on-board RAM 68, and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VV modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
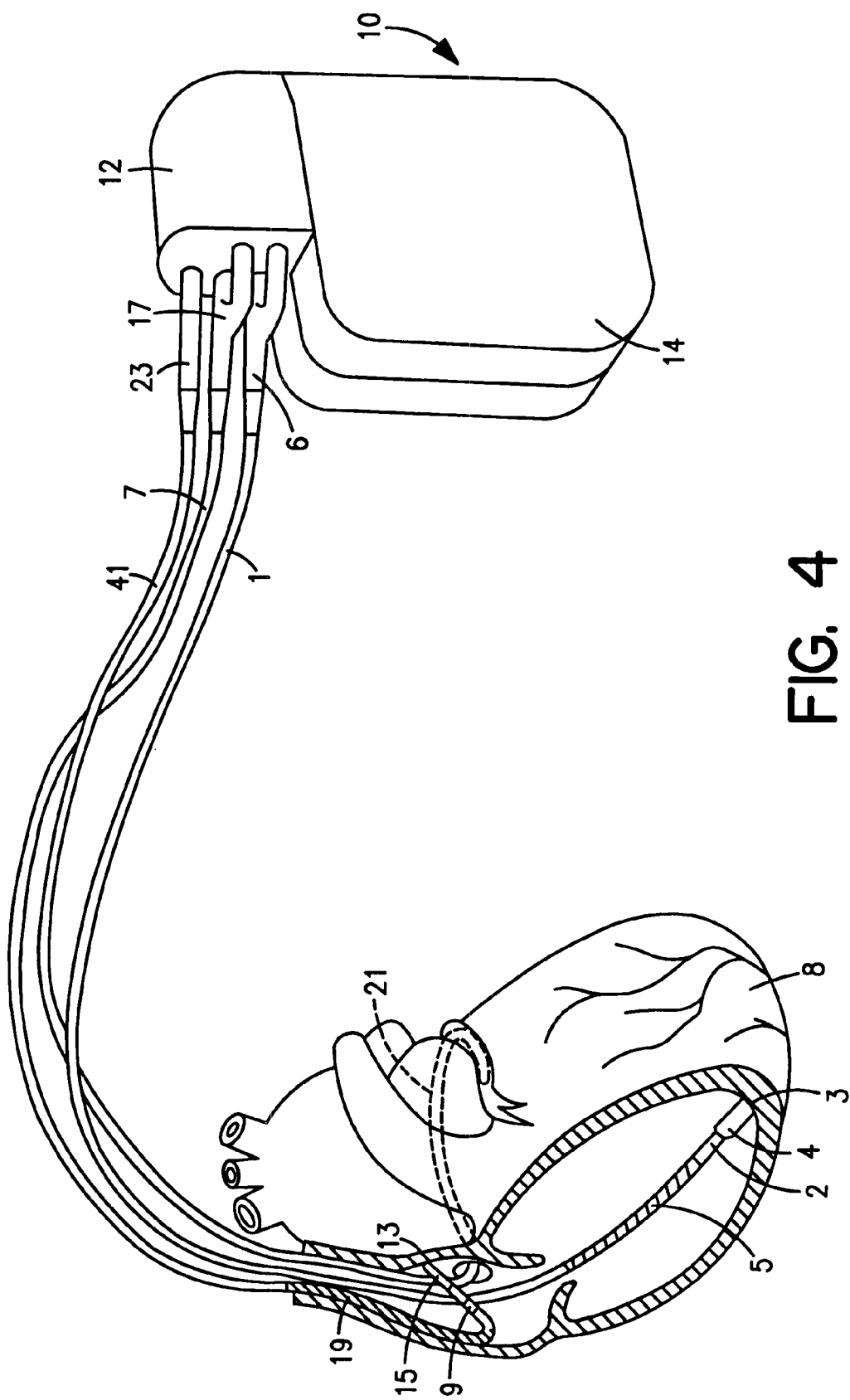
FIG. 4 illustrates another embodiment of the implantable medical device of FIG. 1, made in accordance with the present invention.
Figure 5:
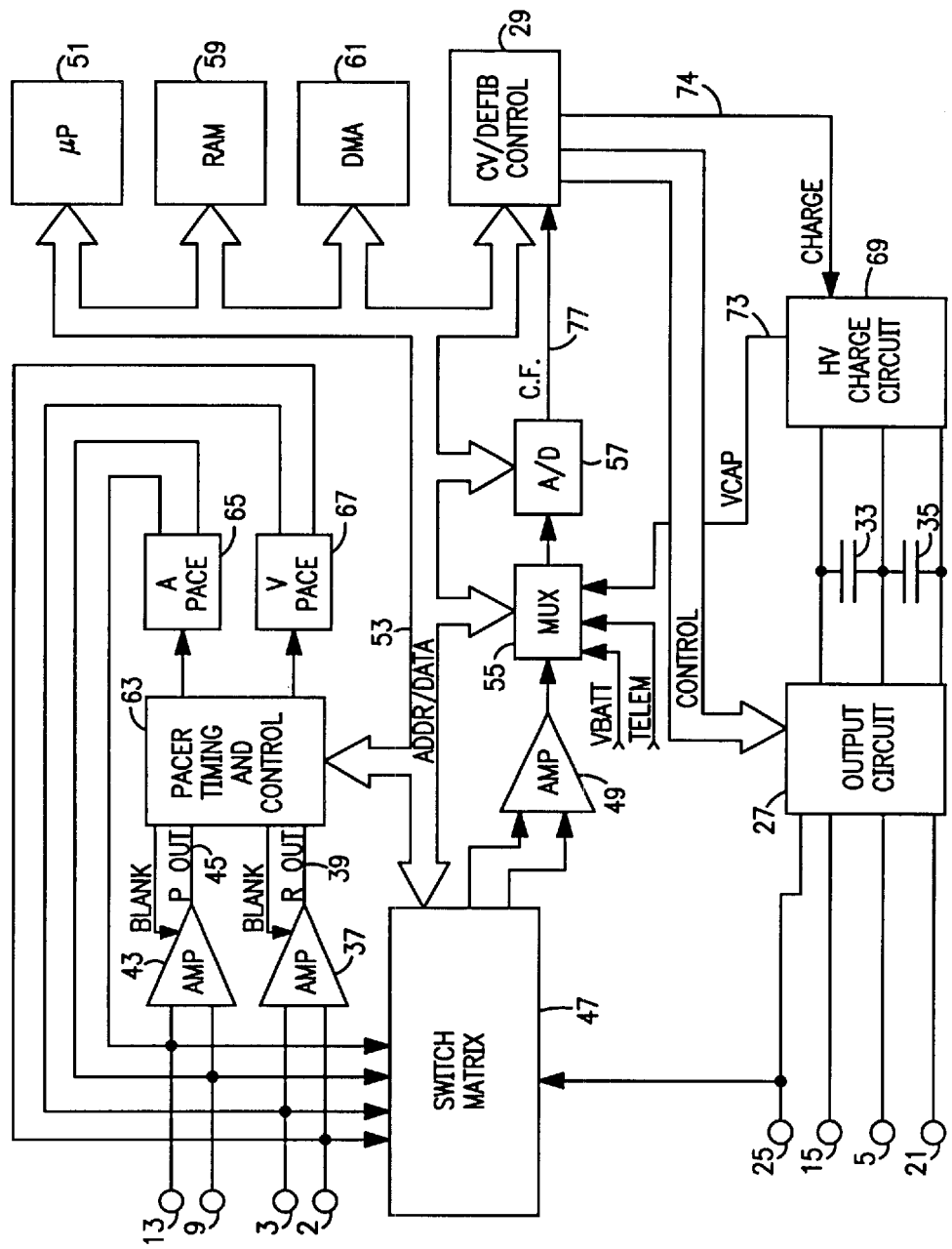
FIG. 5 illustrates a block diagram of the embodiment of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the processor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM 59 under control of direct memory access circuit 61. Microprocessor 51 may employ digital signal analysis techniques to characterize the digitized signals stored in RAM 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by processor 51, in response to stored data in memory 59 and are communicated to pacing circuitry 63 via address/data bus 53. Pacer circuitry 63 also determines the amplitude of the cardiac pacing pulses under control of processor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by processor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by processor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press,* pp. 167–170, also hereby incorporated by reference in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from processor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, processor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, processor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by processor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, processor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a An monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra and in U.S. Pat. No. 4,727,877, both of which are hereby incorporated by reference in their entireties.

An example of circuitry which may be used to control delivery of monophasic pulses is disclosed in U.S. Pat. No. 5,163,427 to Keimel, also hereby incorporated by reference in its entirety. Output control circuitry similar to that disclosed in the '551 Patent or in U.S. Pat. No. 4,800,883 to Winstrom, both of which are hereby incorporated by reference in their entireties, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
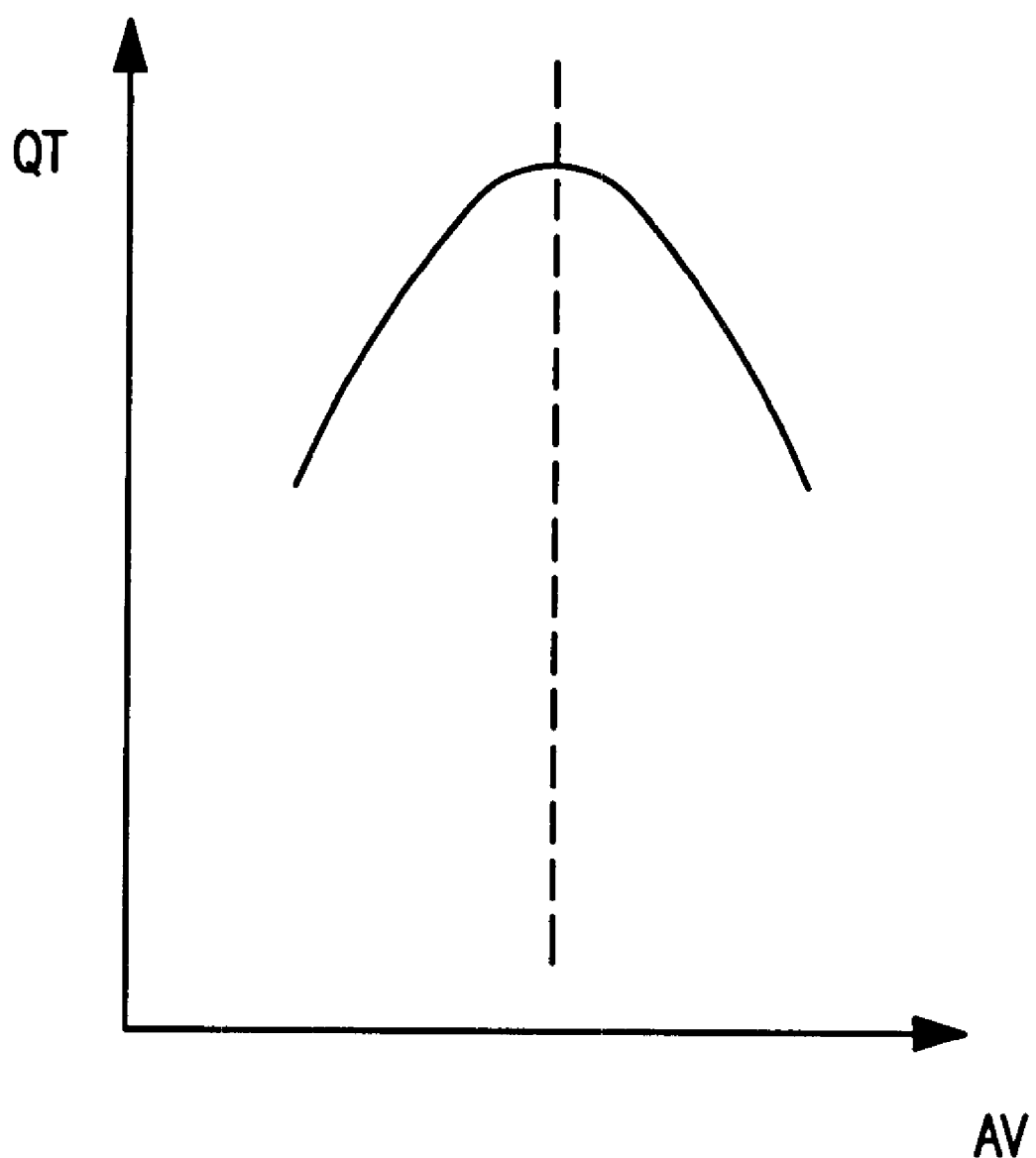
FIG. 6 is a curve illustrating the variation of QT interval versus AV delay for a patient paced in both the atrium and the ventricle at a fixed pacing rate.

FIG. 6 shows a representative graph acquired by varying the AV interval in a patient being paced at a fixed rate in both the atrium and aventricle, and measuring the QT interval corresponding to each AV interval. These curves reflect a statistical fitting to the actual data, and in each case lend to a determination of the peak of the curve, which corresponds to the optimized AV interval. As used herein, the optimum or optimized AV interval corresponds to about the peak of the curve; it is not necessary to find the exact peak in order to gain a significantly improved pacemaker response. Although the invention is illustrated by use of QT as the preferred hemodynamic variable, it is to be understood that other variables may be used within the scope of the invention. Thus, the pacemaker 10 may include means for determining stroke volume, depolarization slope, pre-ejection interval, dp/dt, etc., each of such variables being equivalent to QT as a hemodynamic variable used in this invention.

Figure 7:
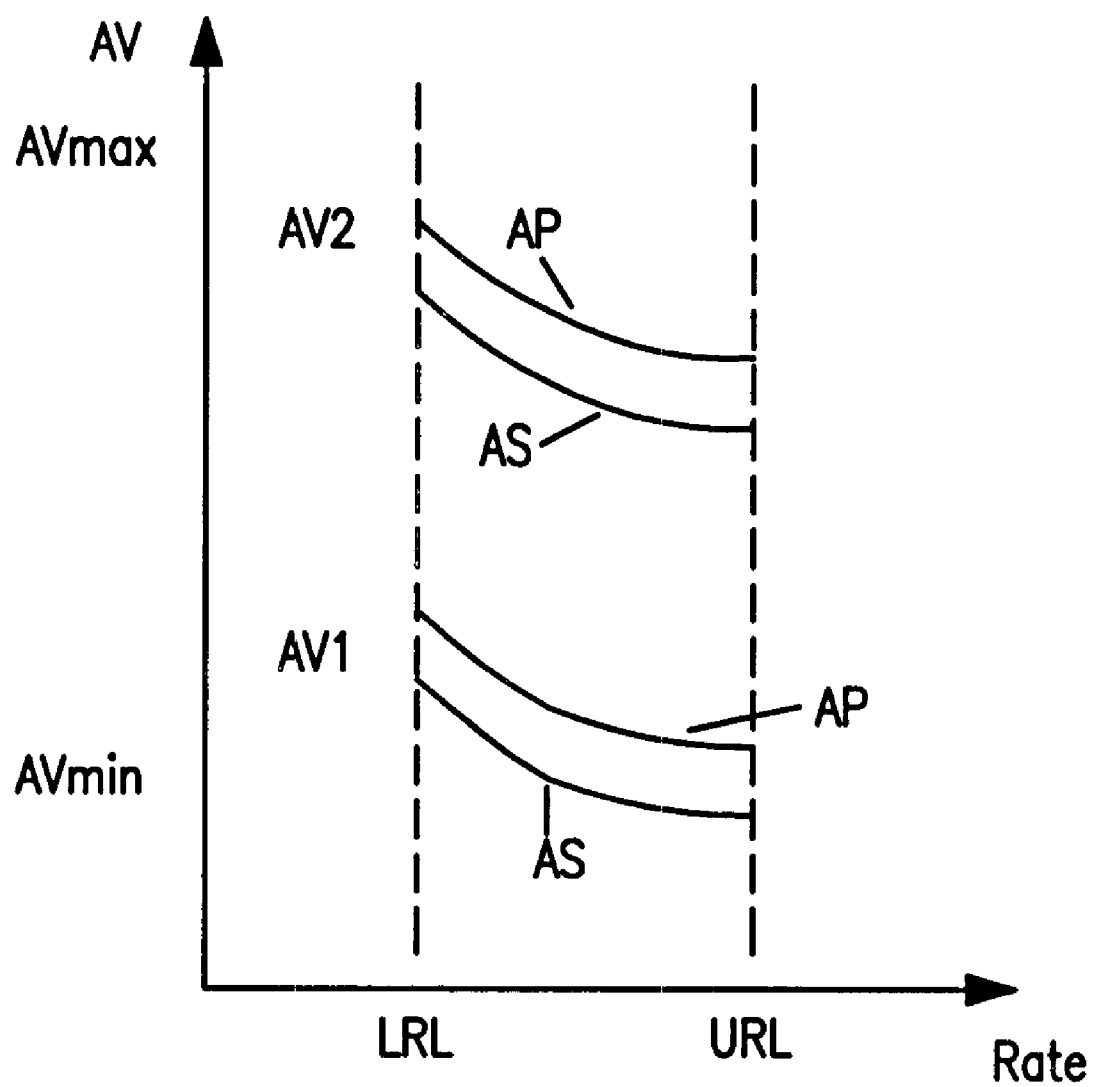
FIG. 7 is a representation of curves showing the relationship between AV interval and heart rate.

Assuming that a test is performed resulting in data as represented in FIG. 6, the optimized AV interval data can be used to adjust the AV interval used in dual chamber pacing. As discussed above, AV interval may preferably be a function of atrial rate, i.e., AV=f(rate). In FIG. 7, rate is plotted on the horizontal axis, and AV interval is plotted on the vertical axis. The pacemaker 10 is preferably programmed with a predetermined $AV_{min}$ and predetermined $AV_{max}$, and the AV=f(rate) curve is positioned between the rate limits of LRL and URL. In FIG. 7, a first solid line is shown, which may be illustrative of AV=f(rate) before the test. For this curve, AV at LRL is shown as $AV_1$. Assuming that the test is done at LRL, a new optimized value of $AV_2$ is determined at LRL, and shown by a second solid line indicating that the optimized AV at LRL is a lower value. In a simplified arrangement, the slope of the curve between the rate limits of LRL and URL may be held the same, such that the new curve is determined by repositioning of the value at LRL. Other more complex modifications are within the scope of the invention. Still referring to FIG. 2, dashed lines are shown which represent curves of $AV_s$=f(rate), where $AV_s$ is the value of AV to be used following an AS for the embodiment where different values are used following atrial sense and atrial pace events.

The above-described test measures the entire AV versus QT curve (FIG. 6). This requires a long measurement period. A simpler and faster method is to change the AV delay to one step (e.g. step of 25 ms) longer and one step shorter than the presently active value. If during one of these steps a longer QT interval is measured, the active AV delay should be changed by one step (could be a different step size) in that direction. If the presently active AV delay has the optimal value, both measurements will yield a shorter QT interval and therefore no adaption is necessary. It is preferable that the presently active AV delay value only be adapted by a single step per measurement (per day). This avoids large variations in the event that, for whatever reason, a measurement yields incorrect information.

As described above, the QT interval may be used to determine the hemodynamically optimal AV delay. In accordance with the present invention, the following table (Table 2) illustrates that the difference in QT intervals is significantly larger in patients with a low left ventricular ejection function (LVEF) than in patients with a higher LVEF. Preferably, this occurs when making an inter-patient comparison of the longest and shortest QT intervals over the same range of AV delays.

TABLE 2

|  | EF > 60% | EF > 45% | p |
|---|---|---|---|
| Longest QT | 333 ± 14 | 374 ± 19 | 0.004 |
| Shortest QT | 329 ± 16 | 367 ± 20 | 0.009 |

TABLE 2-continued

|  | EF > 60% | EF > 45% | p |
|---|---|---|---|
| QT Difference | 4 ± 4 | 7 ± 2 |  |
| p (longest/shortest) | 0.027 | 0.002 |  |

The data in Table 2 therefore suggests that the difference in QT intervals, measured over the same range of AV delays, is a measure of the LVEF. That is, the left ventricular function may be characterized by measuring the AV delay dependency of the QT interval. This suggestion also seems logical from a pragmatic point of view: patients with a low LVEF will be more sensitive to factors that further deteriorate their cardiac output.

Figure 8:
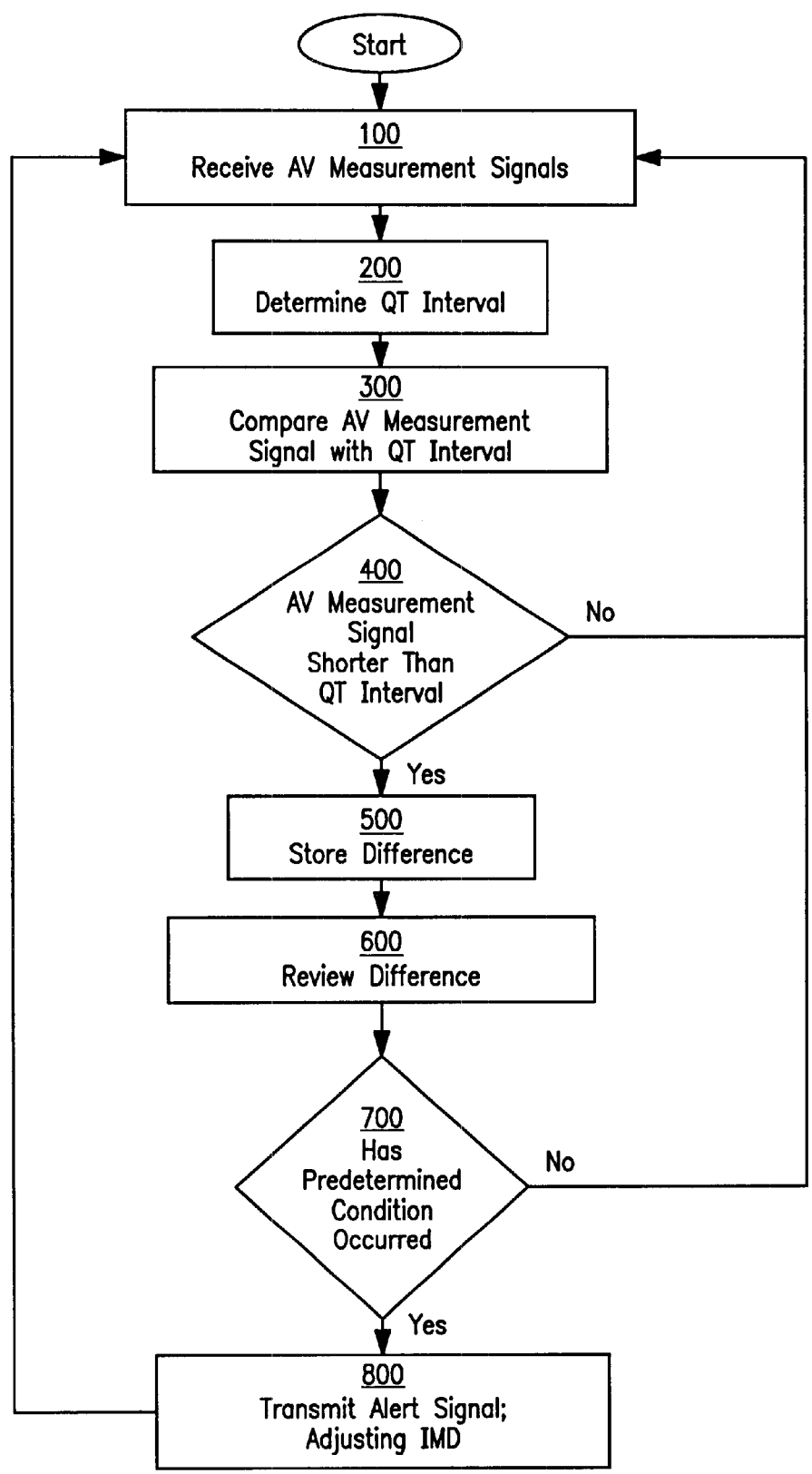
FIG. 8 is a flowchart illustrating a method for operating an implantable medical device.

FIG. 8 illustrates a flow chart detailing a method of operating an implantable medical device, in accordance with the present invention. In Block 100, the processor 64 of the IMD 10 receives a plurality of AV measurement signals. AV measurement signals correspond to the time elapsed between the commencement of a contraction of a ventricle of a mammalian heart 8 and the termination of a relaxation of that ventricle. Preferably, the AV measurement signals are sensed by the sensing lead 7 in the mammalian heart 8, and are transmitted to the processor 64.

After receiving the AV measurement signals, the processor 64 then determines a QT interval, as illustrated in Block 200. Preferably, the QT interval is based on the AV measurement signals received from the sensing lead 7. Furthermore, determination of QT interval is done in any standard manner, such as those described above.

In Block 300, the processor 64 compares each of the AV measurement signals with the QT interval to determine which AV measurement signal, if any, is shorter than the QT interval. If no AV measurement signal is shorter than the QT interval (as determined in Block 400), the processor 64 returns to Block 100 to receive the next AV measurement signal. When this happens, the processor will preferably readjust the QT interval in accordance with the next AV measurement signal received. If an AV measurement signal is shorter than the QT interval, the processor 64, in Block 500, stores, in a memory location, such as, for example, a RAM location 68, the difference between the AV measurement signal and the QT interval. This storing of differences of AV measurement signals allows the IMD 10 to build a long term trend monitor of the difference in the QT interval/AV measurement signal relationship. This long term trend, which may be referred to as a predetermined condition, is discussed below.

In Block 600, the processor 64 then reviews each of the stored differences. Preferably, the processor 64 is predetermined to review each of the stored differences after a preset number of differences are recorded. Alternatively, the processor may review the stored differences at a preset time period, such as, for example, every week.

In Block 700, the processor 64 determines whether a predetermined condition has occurred. Preferably, the predetermined condition occurs when there has been an increasing trend in either the number of stored differences or the values of each of the differences, over a predetermined period of time.

If a predetermined condition has not occurred, the processor 64 returns to Block 100 to receive the next AV measurement signal. If a predetermined condition has occurred, the processor then transmits an alert signal (Block 800). Alternatively or conjunctively with the transmission of the alert signal, the processor 64 may adjust the synchronicity of the IMD 10.

This predetermined condition (essentially a long term trend of the QT/AV relationship) reflects LVEF functions, as described above, and provides important diagnostic data which may be used by a physician to monitor progress of a heart condition (such as, for example, heart failure). Additionally, the predetermined condition may monitor the effectiveness of the provided therapy, e.g., drug therapy or multi-site pacing.

In addition, such information regarding the LVEF may be used to optimize parameters in a pacing device that provides therapy to patients, e.g., in a bi-ventricular configuration. Bi-ventricular pacing may be applied in an atrial-driven or ventricular-only mode. This may depend on the atrial rhythm status: when chronic atrial fibrillation is present, the latter may be chosen. In other patients, an atrial synchronous mode may be the pacing mode of choice. Parameters that may be automatically optimized on the basis of a parameter that reflects left ventricular function information may include the LV-RV delay and/or the RA-LV delay, both as described above.

The invention has been illustrated by a system which measures QT interval as the hemodynamic variable that is compared to AV interval, but other hemodynamic variables are equally useful and within the scope of the invention. Thus, as with the QT interval, any variable can be used so long as change in the variable can be substantially attributable to change in AV interval.

The preceding specific embodiments are illustrative of the practice of the invention. It is to be understood, therefore, that other expedients known to those skilled in the art or disclosed herein, may be employed without departing from the invention or the scope of the appended claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All printed publications, patent applications and patents referenced hereinabove are incorporated by reference herein, each in its entirety.

We claim:

1. A method of operating an implantable medical device, comprising:

receiving a plurality of atrio-ventricular (AV) measurement signals;

determining a QT interval as a function of the AV measurement signals;

comparing each of the plurality of AV measurement signals with the QT interval; and if one of the plurality of AV measurement signals is less than the QT interval, storing a difference between the one of the plurality of AV measurement signals and the QT interval.

2. The method of claim 1, further comprising reviewing the differences after a predetermined time period.

3. The method of claim 2, further comprising transmitting an alert signal if the differences indicates a predetermined condition.

4. The method of claim 3, wherein the alert signal comprises an audible signal.

5. The method of claim 3, wherein the alert signal comprises a radio signal.

6. The method of claim 3, wherein the predetermined condition comprises an increase in the value of the differences over the predetermined time period.

7. The method of claim 3, further comprising adjusting the synchronization of the implantable medical device after transmitting the alert signal.

8. The method of claim 1, wherein each of the plurality of AV measurement signals is compared to an adjusted QT interval.

9. The method of claim 8, wherein the adjusted QT interval comprises an adjustment to the QT interval based on each of the plurality of AV measurement signals.

10. The method of claim 1, wherein each of the plurality of AV measurement signals comprises the time elapsed between the commencement of a contraction of a ventricle of a mammalian heart and the termination of a relaxation of the ventricle.

11. An implantable medical device, comprising:
a processor;
a memory location operably connected to the processor; and
at least one sensing lead operably connected to the processor;
wherein
a difference between one of a plurality of atrio-ventricular (AV) measurement signals sent by the at least one sensing lead and a QT interval is stored in the memory location for each of the plurality of AV measurement signals received by the processor that is shorter than the QT interval.

12. The implantable medical device of claim 11, wherein the processor further reviews the differences after a predetermined time period.

13. The implantable medical device of claim 12, wherein the processor further transmits an alert signal if the differences indicates a predetermined condition.

14. The implantable medical device of claim 13, wherein the alert signal comprises an audible signal.

15. The implantable medical device of claim 13, wherein the alert signal comprises a radio signal.

16. The implantable medical device of claim 13, wherein the predetermined condition comprises an increase in the value of the differences over the predetermined time period.

17. The implantable medical device of claim 13, wherein the processor further adjusts the synchronization of the implantable medical device after transmitting the alert signal.

18. The implantable medical device of claim 11, wherein each of the plurality of AV measurement signals is compared to an adjusted QT interval.

19. The implantable medical device of claim 18, wherein the adjusted QT interval comprises an adjustment to the QT interval based on each of the plurality of AV measurement signals.

20. The implantable medical device of claim 11, wherein each of the plurality of AV measurement signals comprises the time elapsed between the commencement of a contraction of a ventricle of a mammalian heart and the termination of a relaxation of the ventricle.

21. An implantable medical device system, comprising:
means for receiving a plurality of atrio-ventricular (AV) measurement signals;
means for determining a QT interval as a function of the AV measurement signals;
means for comparing each of the plurality of AV measurement signals with the QT interval; and
means for storing a difference between the one of the plurality of AV measurement signals and the QT interval when one of the plurality of AV measurement signals is less than the QT interval.

22. The implantable medical device system of claim 21, further comprising means for reviewing the differences after a predetermined time period.

23. The implantable medical device system of claim 22, further comprising means for transmitting an alert signal if the differences indicates a predetermined condition.

24. The implantable medical device system of claim 23, wherein the alert signal comprises an audible signal.

25. The implantable medical device system of claim 23, wherein the alert signal comprises a radio signal.

26. The implantable medical device system of claim 23, wherein the predetermined condition comprises an increase in the value of the differences over the predetermined time period.

27. The implantable medical device system of claim 23, further comprising means for adjusting the synchronization of the implantable medical device after transmitting the alert signal.

28. The implantable medical device system of claim 21, wherein each of the plurality of AV measurement signals is compared to an adjusted QT interval.

29. The implantable medical device system of claim 28, wherein the adjusted QT interval comprises an adjustment to the QT interval based on each of the plurality of AV measurement signals.

30. The implantable medical device system of claim 21, wherein each of the plurality of AV measurement signals comprises the time elapsed between the commencement of a contraction of a ventricle of a mammalian heart and the termination of a relaxation of the ventricle.

31. A method of operating an implantable medical device, comprising:
providing a QT interval;
receiving a first atrio-ventricular (AV) measurement signal;
comparing the first AV measurement signal to the QT interval; and
if the first AV measurement signal is less than the QT interval, storing a first difference between the first AV measurement signal and the QT interval.

32. The method of claim 31, further comprising adjusting the QT interval after receiving the first AV measurement signal.

33. The method of claim 32, further comprising receiving a second AV measurement signal.

34. The method of claim 33, further comprising comparing the second AV measurement signal to the adjusted QT interval.

35. The method of claim 34, further comprising storing a second difference between the second AV measurement signal and the QT interval if the second AV measurement signal is less than the QT interval,.

36. The method of claim 35, further comprising reviewing each of the differences after a predetermined time period.

37. The method of claim 36, further comprising transmitting an alert signal if each of the differences indicates a predetermined condition.

38. The method of claim 37, wherein the alert signal comprises an audible signal.

39. The method of claim 37, wherein the alert signal comprises a radio signal.

40. The method of claim 37, wherein the predetermined condition comprises an increase in the value of each of the differences over the predetermined time period.

41. The method of claim 37, further comprising adjusting the synchronization of the implantable medical device after transmitting the alert signal.

42. The method of claim 31, wherein the first AV measurement signal comprises the time elapsed between the commencement of a contraction of a ventricle of a mammalian heart and the termination of a relaxation of the ventricle.

* * * * *